United States Patent

Geissler et al.

Patent Number: 6,084,114
Date of Patent: Jul. 4, 2000

[54] DIPALLADAPHOSPHACYCLOBUTANES AND A PROCESS FOR PREPARING THE SAME

[75] Inventors: Holger Geissler, Mainz; Peter Gross, Kelsterbach; Bianca Guckes, Waldems, all of Germany

[73] Assignee: Aventis Research & Technologies GmbH & Co. KG, Frankfurt, Germany

[21] Appl. No.: 09/308,259

[22] PCT Filed: Nov. 13, 1997

[86] PCT No.: PCT/EP97/06327

§ 371 Date: Jul. 19, 1999

§ 102(e) Date: Jul. 19, 1999

[87] PCT Pub. No.: WO98/22485

PCT Pub. Date: May 28, 1998

[30] Foreign Application Priority Data

Nov. 18, 1996 [DE] Germany .................. 196 47 584

[51] Int. Cl.⁷ .................. C07F 9/02; C07F 15/00
[52] U.S. Cl. .................. 556/21; 556/16; 556/22; 556/23; 556/136; 502/155; 502/162
[58] Field of Search .................. 556/16, 21, 22, 556/23, 136; 502/155, 162

[56] References Cited

U.S. PATENT DOCUMENTS 5,831,107  11/1998  Beller er al. .................. 556/16

FOREIGN PATENT DOCUMENTS 0 688 779 A1  12/1995  European Pat. Off. .

OTHER PUBLICATIONS

Werner et al., "Intramolecular Metalation of PBut2PH and PBut3 in Palladium Acetate Complexes", Journal of Organometallic Chemistry, vol. 204, 1981, pp. 415–422.

Goel et al., "Isolation and Characterization of an Unusual Mixed Methoxy– and Chloro–bridged Dinuclear Palladium Complex", Transition Met. Chem., vol. 5(6), 1980, pp. 378–379.

Clark et al., "Facile Intramolecular Metalation of Tri–tert–butylphosphine in Palladium(II) Hydride Complexes", Journal of Organometallic Chemistry, vol. 166(2), 1979, pp. 2803–2808.

Clark et al., "Solvent Effects on the Metalation of Tri–tert-butylphosphine, Preparation and Characterizatio of 'PtPBu2tC(CH3)2CH2C1!2 and 'pdPBu2tC(CH3)2CH2CL!2", Inorganica Chimica Acta, vol. 31(2), 1978, pp. L441–442.

Clark et al., "Facile Intramolecular Metalation of Tri–tert–butylphosphine in Palladaium(II) Hydride Complexes", Journal or Organometallic Chemistry, 1979, pp. C29–C32.

*Primary Examiner*—Porfirio Nazario-Gonzalez
*Attorney, Agent, or Firm*—Frommer, Lawrence & Haug LLP

[57] ABSTRACT

The invention relates to palladaphosphacyclobutanes of the formula (I)

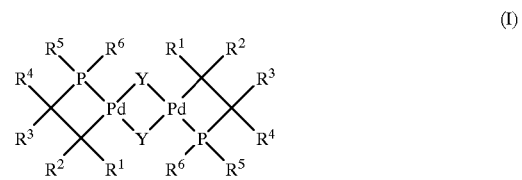

where $R^1$, $R^2$ are, independently of one another, hydrogen, $(C_1-C_4)$-alkyl, $(C_3-C_{12})$-cycloalkyl, $(C_1-C_4)$-alkoxy, fluorine, $N[(C_1-C_4)\text{-alkyl}]_2$, $CO_2\text{-}(C_1-C_4)$-alkyl, $OCO\text{-}(C_1-C_4)$-alkyl or aryl;

$R^3$, $R^4$, $R^5$, $R^6$ are, independently of one another, $(C_1-C_8)$-alkyl, $(C_3-C_{12})$-cycloalkyl or aryl;

or where $R^1$ and $R^2$, $R^1$ or $R^2$ and $R^3$ or $R^4$, $R^3$ and $R^4$, $R^3$ or $R^4$ and $R^5$ or $R^6$, or $R^5$ and $R^6$ together form an aliphatic ring; or where $R^5$ and $R^6$, $R^3$ or $R^4$ and $R^5$ or $R^6$ together form an aromatic ring; and Y is an anion of an inorganic or organic acid, with the exception of the compounds di-$\mu$-chloro-bis[2-[bis(1,1-dimethylethyl)phosphino]-2-methylpropyl-C,P]dipalladium(II)

di-$\mu$-bromo-bis[2-[bis(1,1 -dimethylethyl)phosphino]-2-methylpropyl-C,P]dipalladium(II)

di-$\mu$-trifluoroacetato-bis[2-[bis(1,1 -dimethylethyl) phosphino]-2-methylpropyl-C,P]dipalladium(II)

di-$\mu$-chloro-bis[2-[(1,1 -dimethylethyl)phenylphosphino]-2-methylpropyl-C,P]dipalladium(II)

$\mu$-chloro-$\mu$-methoxy-bis[2-[bis(1,1 -dimethylethyl) phosphino]-2-methylpropyl-C,P]dipalladium(II).

16 Claims, No Drawings

DIPALLADAPHOSPHACYCLOBUTANES AND A PROCESS FOR PREPARING THE SAME

The present invention relates to new palladaphosphacyclobutanes and a process for their preparation.

Palladaphosphacyclobutanes play an important role as catalysts for a number of processes. Examples of such processes are the synthesis of substituted styrenes, stilbenes and cinnamic acids from aryl halides.

The literature discloses the following compounds of this type:
1. Di-$\mu$-chloro-bis[2-[bis(1,1-dimethylethyl)phosphino]-2-methylpropyl-C,P]dipalladium(II); H. C. Clark et al., Inorg. Chim. Acta 31, (1978), L441–L442; H. C. Clark et al. J. Organomet. Chem. 166, (1979) C29–C32, H. C. Clark et al., Inorg. Chem. 18, (1979), 2803–2808
2. Di-$\mu$-bromo-bis[2-[bis(1,1-dimethylethyl)phosphino]-2-methylpropyl-C,P]dipalladium(II); H. C. Clark et al., J. Organomet. Chem. 166, (1979) C29–C32; H. C. Clark et al., Inorg. Chem. 18, (1979), 2803–2808
3. Di-$\mu$-trifluoroacetato-bis[2-[bis(1,1-dimethylethyl)phosphino]-2-methylpropyl-C,P]dipalladium(II); H. C. Clark et al., J. Organomet. Chem. 166, (1979) C29–C32; H. C. Clark et al., Inorg. Chem. 18, (1979), 2803–2808
4. Di-$\mu$-chloro-bis[2-[(1,1-dimethylethyl)phenylphosphino]-2-methylpropyl-C,P]dipalladium(II); H. Werner et al., J. Organomet. Chem. 204, (1980), 415–422
5. $\mu$-Chloro-$\mu$-methoxy-bis[2-[bis(1,1-dimethylethyl)phosphino]-2-methylpropyl-C,P]dipalladium(II); A. B. Goel et al., Trans. Met. Chem 5, (1980), 378–379

In J. Chem. Soc. (A) (1971), 2976–2980, Shaw describes the addition of tert-butylphosphines of the formula $P(t-Bu)_n R_{3-n}$ onto palladium(II) compounds to give the corresponding complexes of the formula $Pd(P(t-Bu)_n R_{3-n})_2 X_2$ and $Pd_2(P(t-Bu)_n R_{3-n})_2 X_4$. In the synthesis, the palladaphosphacyclobutanes of the present invention are not obtained.

In Inorg. Chim. Acta 31, (1978), L441–L442, Clark describes the reaction of $PdCl_2(NCPh)_2$ with two equivalents of $P(t-Bu)_3$ to give the corresponding palladaphosphacyclobutane in 70% yield. This process employs the toxicologically dubious solvent methylene chloride in which both the starting material and the product are soluble. To isolate this palladaphosphacyclobutane, the solvent is taken off, the product is extracted with benzene and subsequently precipitated by addition of hexane. Owing to the use of two equivalents of $P(t-Bu)_3$ per equivalent of palladium and the use of methylene chloride and benzene, the process is ecologically and economically disadvantageous.

In Inorg. Chim. Acta 31, (1978), L441–L442, Clark describes the reaction of $K_2PdCl_4$ with two equivalents of $P(t-Bu)_3$ to give the corresponding palladaphosphacyclobutane in 72% yield. In this process, dimethylformamide is used as solvent. To isolate this palladaphosphacyclobutane, the solvent is taken off and the product is precipitated by addition of ethanol. In Organometallics 1, (1982), 658–666, Clark describes an analogous process in which $Na_2PdCl_4$ and three equivalents of $P(t-Bu)_3$ are used as starting materials and the corresponding palladaphosphacyclobutane is obtained in 75% yield. Owing to the use of two or three equivalents of $P(t-Bu)_3$ per equivalent of palladium, both processes are ecologically and economically disadvantageous.

In Inorg. Chem. 18, (1979), 2803–2808, Clark describes the reaction of $PdCl_2(NCPh)_2$ with one equivalent of $P(t-Bu)_3$ to give the corresponding palladaphosphacyclobutane without indicating the yield. This process employs the toxicologically dubious solvent methylene chloride in which both the starting material and the product are soluble. To isolate this palladaphosphacyclobutane, the solvent is taken off, the product is extracted with benzene and subsequently precipitated by addition of hexane. Owing to the use of methylene chloride and benzene, the process is ecologically and economically disadvantageous.

In J. Organomet. Chem. 204, (1980) 415–422, Werner describes the reaction of $Pd(P(t-Bu)_3)_2Cl_2$ and $Pd(P(t-Bu)_2Ph)_2Cl_2$ with silver acetate to prepare the corresponding palladaphosphacyclobutanes, di-$\mu$-chloro-bis[2-[bis(1,1-dimethylethyl)phosphino]-2-methylpropyl-C,P]dipalladium (II) and di-$\mu$-chloro-bis[2-[(1,1-dimethylethyl)phenylphosphino]-2-methylpropyl-C,P]dipalladium(II). Owing to the use of two equivalents of phosphine per equivalent of palladium and the use of silver acetate in stoichiometric amounts, this process is ecologically and economically very disadvantageous.

In Trans. Met. Chem 5, (1980), 378–379, Goel describes the reaction of the methanol-insoluble di-$\mu$-chloro-bis[2-[bis(1,1-dimethylethyl)phosphino]-2-methylpropyl-C,P]dipalladium(II) to give the methanol-soluble $\mu$-chloro-$\mu$-methoxy-bis[2-[bis(1,1-dimethylethyl)phosphino]-2-methylpropyl-C,P]dipalladium(II) in a yield of 70% by suspending the starting material in methanol, subsequently reacting it with one equivalent of sodium hydroxide and evaporating the solvent. The use of a sparingly soluble substance in order to produce a readily soluble one is disadvantageous insofar as the solvent has to be taken off at the end, and this is reflected in the low yield. Since the di-$\mu$-chloro-bis[2-[bis(1,1-dimethylethyl)phosphino]-2-methylpropyl-C,P]dipalladium(II) has to be prepared first for this reaction, this is a two-stage synthesis compared to the above-described syntheses, which is a further disadvantage.

In view of the many possible uses of palladaphosphacyclobutanes, there is a need for new palladaphosphacyclobutanes in order, on the one hand, to supplement and expand the range of their possible applications and, on the other hand, to enable certain reactions to be carried out particularly advantageously. Likewise, there is also a great need for a simpler process for preparing palladaphosphacyclobutanes of the formula (I).

This object is achieved by the palladaphosphacyclobutanes of the invention.

The invention provides palladaphosphacyclobutanes of the formula (I)

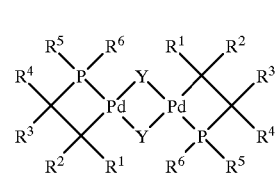

(I)

where
$R^1$, $R^2$ are, independently of one another, hydrogen, $(C_1-C_4)$-alkyl, $(C_3-C_{12})$-cycloalkyl, $(C_1-C_4)$-alkoxy, fluorine, $N[(C_1-C_4)$-alkyl$]_2$, $CO_2$-$(C_1-C_4)$-alkyl, $OCO$-$(C_1-C_4)$-alkyl or aryl;
$R^3$, $R^4$, $R^5$, $R^6$ are, independently of one another, $(C_1-C_8)$-alkyl, $(C_3-C_{12})$-cycloalkyl or aryl; or where $R^1$ and $R^2$, $R^1$ or $R^2$ and $R^3$ or $R^4$, $R^3$ and $R^4$, $R^3$ or $R^4$ and $R^5$ or $R^6$, or $R^5$ and $R^6$ together form an aliphatic ring having from 4 to 10 carbon atoms;

or where R⁵ and R⁶, R³ or R⁴ and R⁵ or R⁶ together form an aromatic ring having from 5 to 9 carbon atoms; and Y is an anion of an inorganic or organic acid, with the exception of the compounds di-μ-chloro-bis[2-[bis(1,1-dimethylethyl)phosphino]-2-methylpropyl-C,P]dipalladium(II)

di-μ-bromo-bis[2-[bis(1,1-dimethylethyl)phosphino]-2-methylpropyl-C,P]dipalladium(II)

di-μ-trifluoroacetato-bis[2-[bis(1,1-dimethylethyl)phosphino]-2-methylpropyl-C,P]dipalladium(II)

di-μ-chloro-bis[2-[(1,1-dimethylethyl)phenylphosphino]-2-methylpropyl-C,P]dipalladium(II)

μ-chloro-μ-methoxy-bis[2-[bis(1,1-dimethylethyl)phosphino]-2-methylpropyl-C,P]dipalladium(II).

Preference is given to palladaphosphacyclobutanes of the formula (I), in which $R^1$, $R^2$ are, independently of one another, phenyl, $R^5$, $R^6$ are, independently of one another, phenyl, naphthyl or anthracenyl which may each be substituted by from 1 to 3 ($C_1$–$C_4$)-alkyl or from 1 to 3 ($C_1$–$C_4$)-alkoxy groups.

Particular preference is given to palladaphosphacyclobutanes of the formula (I), in which $R^3$, $R^4$ are, independently of one another, phenyl, $R^5$, $R^6$ are, independently of one another, o-trifluoromethylphenyl, o-trifluoromethyl-p-tolyl, o-trifluoromethyl-p-methoxyphenyl, o-methoxyphenyl, o,p-dimethoxyphenyl, o,o,p-trimethoxy-phenyl, tert-butyl, n-butyl, isopropyl, isobutyl, cyclohexyl, 1-methylcyclohexyl.

Particularly important compounds are di-μ-acetato-bis[2-[bis(1,1-dimethylethyl)phosphino]-2-methylpropyl-C,P]dipalladium(II)

di-μ-acetato-bis[2-[(1,1-dimethylethyl)phenylphosphino]-2-methylpropyl-C,P]dipalladium(II)

di-μ-chloro-bis[2-[bis(1,1-dimethylethyl)phosphino]-2-methylpropyl-C,P]dipalladium(II)

di-μ-chloro-bis[2-[(1,1-dimethylethyl)phenylphosphino]-2-methylpropyl-C,P]dipalladium(II)

di-μ-bromo-bis[2-[bis(1,1-dimethylethyl)phosphino]-2-methylpropyl-C,P]dipalladium(II)

di-μ-bromo-bis[2-[(1,1-dimethylethyl)phenylphosphino]-2-methylpropyl-C,P]dipalladium(II)

The palladaphosphacyclobutanes of the invention are a new class of catalysts. Their catalytic activity in the olefination of aryl halides is extraordinary compared to the prior art so that there is great industrial interest in the compounds of the invention.

The invention further provides a process for preparing compounds of the formula (I), which comprises reacting a phosphine of the formula (II)

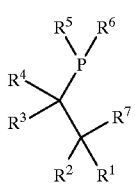

(II)

where $R^1$ to R6 are as defined above and $R^7$ is hydrogen or deuterium, with a palladium salt of the formula (III), a palladium complex of the formula (IV) or an alkali metal palladate of the formula (V)

Pd Y₂ (III)

Pd Y₂L₂ (IV)

M₂[PdY₄] (V)

where Y is as defined above, M is sodium, potassium or lithium and L is 1,5-cyclooctadiene, acetonitrile or benzonitrile, in the presence of an organic solvent.

In many cases it has been found useful to carry out the reaction at a temperature of from 0° to 160° C., preferably from 0° to 150° C., in particular from 5 to 140° C.

The phosphine of the formula (II) and the palladium compound of the formula (III), (IV) or (V) are used in a molar ratio of phosphine to Pd compound of from 0.1 to 20, in particular from 0.15 to 15, preferably from 0.2 to 10, particularly preferably from 0.8 to 1.2.

Suitable solvents are aliphatic hydrocarbons and aromatic hydrocarbons. Toluene or xylenes are very suitable.

For the preparation of sparingly soluble palladaphosphacyclobutanes, it is also possible to react a more readily soluble palladacycle with the corresponding anion of an organic or inorganic acid.

The following examples illustrate the invention:

EXAMPLE 1

Di-μ-acetato-bis[2-[bis(1,1-dimethylethyl)phosphino]-2-methylpropyl-C,P]dipalladium(II)

5.1g (22.7 mmol) of Pd(OAc)₂ are dissolved in 200 ml of toluene. The solution is admixed with 5 g (24.7 mmol) of tri(tert-butyl)phosphine. The solution which clears rapidly to a light orange color is heated at 70–80° C. for 10 minutes and then cooled to room temperature. The solvent is removed under reduced pressure. After addition of 200 ml of hexane, the product, di-μ-acetato-bis[2-[bis(1,1-dimethylethyl)phosphino]-2-methyl-propyl-C,P] dipalladium, crystallizes out after a short time and is filtered off. This gives 6.15 g (80% of theory, based on Pd(OAc)₂) of product as a white solid. Recrystallization from hexane and filtration of the solutions through Celite® enables the product to be obtained analytically pure in the form of white crystalline needles.

Elemental analysis: $C_{28}H_{58}O_4P_2Pd_2$ (733.51): found: C, 45.6 %; H, 7.7%; calc.: C, 45.85%; H, 7.97%;

¹H-NMR (300 MHz, CDCl₃):δ=1.88 (3H, s, CH₃); 1.50 (d, 18H, CH₃, ⁴J(PH)=14 Hz); 1.44 (d, 12H, CH₃, ⁴J(PH)= 15 Hz); 1.07 (2H, S_{broad}, 4H, CH₂); ¹³C{¹H}-NMR (75.4 MHz, −70 C, CD₂Cl₂):δ=181.5 (s, CH₃CO₂); 49.5 (s, PC, J(PC)=20.1 Hz); 37.5 (s, PC, J(PC)=10.6 Hz); 32.3 (s, CH₃ J(PC)=2.9 Hz); 31.1 (s, CH₃); 24.7 (s, CH₃CO₂); 7.2 (s, CH₂, J(PC)=33.6 Hz). ³¹P{¹H}-NMR (121.4 MHz, CDCl₃): =−8.5 (s).

EXAMPLE 2

Di-μ-chloro-bis[2-[bis(1,1-dimethylethyl)phosphino]-2-methylpropyl-C,P]dipalladium(II)

50.0 mg of Pd₂(OAc)₂{CH₂C(CH₃)₂P(t-Bu)₂}₂ are dissolved in 0.5 ml of methanol, admixed with 25 mg of lithium chloride in 0.5 ml of methanol and stirred at room temperature for 5 minutes. After addition of 0.2 ml of water, the fine, white precipitate is filtered off, washed three times with 1 ml of a 1:1 mixture of methanol and water and dried under reduced pressure (90° C., 100 mbar, 1 h). This gives 44.9 mg (98% of theory) of di-μ-chloro-bis[2-[bis(1,1-dimethylethyl) phosphino]-2-methylpropyl-C,P]dipalladium(II) as a white solid of the empirical formula $C_{24}H_{52}Cl_2P_2Pd_2$ (686.34). ¹H-NMR and ³¹P-NMR correspond to Example 4.

EXAMPLE 3

Di-μ-bromo-bis[2-[bis(1,1-dimethylethyl)phosphino]-2-methylpropyl-C,P]dipalladium(II)

50.0 mg of $Pd_2(OAc)_2\{CH_2C(CH_3)_2P(t-Bu)_2\}_2$ are dissolved in 0.5 ml of methanol, admixed with 30 mg of lithium bromide in 0.5 ml of methanol and stirred at room temperature for 5 minutes. The fine, white precipitate is filtered off, washed three times with 1 ml of a 1:1 mixture of methanol and water and dried under reduced pressure (90° C., 100 mbar, 1 h). This gives 51.8 mg (98% of theory) of di-μ-bromo-bis[2-[bis(1,1-dimethylethyl)phosphino]-2-methylpropyl-C,P]dipalladium(II) as a white solid of the empirical formula $C_{24}H_{52}Br_2P_2Pd_2$ (775.24). $^1$H-NMR and 31P-NMR correspond to Example 5.

EXAMPLE 4

Di-μ-chloro-bis[2-[bis(1,1-dimethylethyl)phosphino]-2-methylpropyl-C,P]dipalladium(II)

1.00 g (1.36 mmol) of $Pd_2(OAc)_2\{CH_2C(CH_3)_2P(t-Bu)_2\}_2$ are dissolved in 60 ml of methylene chloride, admixed with 4.00 g (13.6 mmol) of [NBu$_4$]Cl and stirred at room temperature for 1 hour. The solvent is removed under reduced pressure and the residue is taken up in 50 ml of methanol. The fine, yellow precipitate is filtered off, washed three times with 20 ml of methanol and twice with 20 ml of pentane and dried under reduced pressure. This gives 700 mg (75% of theory) of di-μ-chloro-bis[2-[bis(1,1-dimethylethyl)phosphino]-2-methylpropyl-C,P]dipalladium (II) as a white solid.

Elemental analysis: $C_{24}H_{52}Cl_2P_2Pd_2$ (686.34): found: C, 41.8 %; H, 7.4 %; calc.: C, 42.00 %; H, 7.64 %;

$^1$H-NMR (300 MHz, $CDCl_3$):δ=1.56 (d, 18H, $CH_3$, $^4$J(PH)=14 Hz); 1.47 (d, 12H, $CH_3$, $^4$J(PH)=14 Hz); 1.10 (d, 4H, $CH_2$, $^4$J(PH)=3 Hz); $^{13}C\{^1H\}$-NMR (75.4 MHz, −70 C., $CD_2Cl_2$):δ=49.3 (d, P$\underline{C}$, J(PC)=19.6 Hz); 38.0 (d, P$\underline{C}$, J(PC)=10.0 Hz); 32.1 (d, $\underline{C}H_3$, J(PC)=3.2 Hz); 31.0 (s, $\underline{C}H_3$); 11.6 (d, $\underline{C}H_2$, J(PC)=29.4 Hz). $^{31}P\{^1H\}$-NMR (121.4 MHz, $CDCl_3$):=−9.7 (s).

EXAMPLE 5

Di-μ-bromo-bis[2-[bis(1,1-dimethylethyl)phosphino]-2-methylpropyl-C,P]dipalladium(II)

1.90 g (2.60 mmol) of $Pd_2(OAc)_2\{CH_2C(CH_3)_2P(t-Bu)_2\}_2$ are dissolved in 60 ml of methylene chloride, admixed with 7.50 g (23.3 mmol) of [NBu$_4$]Cl and stirred at room temperature for 1 hour. The solvent is removed under reduced pressure and the residue is taken up in 50 ml of methanol. The fine, yellow precipitate is filtered off, washed three times with 20 ml of methanol and twice with 20 ml of pentane and dried under reduced pressure. This gives 1.20 g (60% of theory) of di-μ-bromo-bis[2-(bis(1,1-dimethylethyl)phosphino]- 2-methylpropyl-C,P] dipalladium(II) as a white solid.

$C_{24}H_{52}Br_2P_2Pd_2$ (775.24): found: C, 37.9%; H, 6.5%; calc.: C, 37.18%; H, 6.76%;

$^1$H-NMR (300 MHz, $CDCl_3$): δ=1.57 (d, 18H, $CH_3$, $^4$J(PH)=14 Hz); 1.48 (d, 12H, $CH_3$, $^4$J(PH)=14 Hz); 1.21 (d, 4H, $CH_2$, $^4$J(PH)=3 Hz); $^{13}C\{^1H\}$-NMR (75.4 MHz, −70 C., $CD_2Cl_2$): δ=49.7 (d, P$\underline{C}$, J(PC)=19.3 Hz); 38.3 (d, P$\underline{C}$, J(PC)=9.0 Hz); 32.1 (d, $\underline{C}H_3$, J(PC)=3.5 Hz); 31.2 (s, $\underline{C}H_3$); 13.9 (d, $\underline{C}H_2$, J(PC)=27.3 Hz). $^{31}P\{^1H\}$-NMR (121.4 MHz, $CDCl_3$):=−8.6(s).

The following commercial products were used: Celite®/Aldrich Filter aid based on $SiO_2$.

We claim:

1. A palladaphosphacyclobutane of the formula (1)

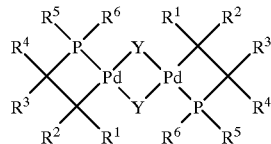

(I)

where

R$^1$, R$^2$ are, independently of one another, hydrogen, $(C_1–C_4)$-alkyl, $(C_3–C_{12})$-cycloalkyl, $(C_1–C_4)$-alkoxy, fluorine, $N[(C_1–C_4)$-alkyl$]_2$, $CO_2$-$(C_1–C_4)$-alkyl, $OCO$-$(C_1–C_4)$-alkyl or aryl;

R$^3$, R$^4$, R$^5$, R$^6$ are, independently of one another, $(C_1–C_8)$-alkyl, $(C_3–C_{12})$ -cycloakyl or aryl;

or where R$^1$, and R$^2$, R$^1$ or R$^2$ and R$^3$ or R$^4$, R$^3$ and R$^4$, R$^3$ or R$^4$ and R$^5$ or R$^6$, or R$^5$ and R$^6$ together form an aliphatic ring having from 4 to 10 carbon atoms;

or where R$^5$ and R$^6$, R$^3$ or R$^4$ and R$^5$ or R$^6$ together form an aromatic ring having from 5 to 9 carbon atoms; and Y is an anion of an inorganic or organic acid, with the exception of the compounds di-μ-chloro-bis[2-[bis(1,1-dimethylethyl) phosphino]-2-methylpropyl-C,P] dipalladium(II)

di-μ-bromo-bis[2-[bis(1,1-dimethylethyl)phosphino]-2-methylpropyl-C,P]dipalladium(11)

di-μ-trifluoroacetato-bis[2-[bis(1,1-dimethylethyl) phosphino]-2-methylpropyl-C,P]dipalladium(11)

di-μ-chloro-bis[2-[(1,1-dimethylethyl)phenylphosphino]-2-methylpropyl-C,P]dipalladium(11)

μ-chloro-μ-methoxy-bis[2-[bis(1,1-dimethylethyl) phosphino]-2-methylpropyl-C,P]dipalladium(11).

2. A palladaphosphacyclobutane as claimed in claim 1, wherein

R$^1$, R$^2$ are, independently of one another, phenyl,

R$^5$, R$^6$ are, independently of one another, phenyl, naphthyl or anthracenyl, which may each be substituted by from 1 to 3 $(C_1–C_4)$-alkyl or from 1 to 3 $(C_1–C_4)$-alkoxy groups.

3. A palladaphosphacyclobutane as claimed in claim 1, wherein

R$^3$, R$^4$ are, independently of one another, phenyl,

R$^5$, R$^6$ are, independently of one another, o-trifluoromethylphenyl, o-trifluoromethyl-p-tolyl, o-trifluoromethyl-p-methoxy-phenyl, o-methoxyphenyl, o,p-dimethoxyphenyl, o,o,p-trimethoxyphenyl, tert-butyl, n-butyl, isopropyl, isobutyl, cyclohexyl, 1-methylcyclohexyl.

4. A palladaphosphacyclobutane as claimed in claim 1, which is di-μ-acetato-bis[2-[bis(1,1-dimethylethyl)phosphino]-2-methylpropyl-C,P]dipalladium(11)

di-μ-acetato-bis[2-[(1,1-dimethylethyl)phenylphosphino]-2-methylpropyl-C,P]dipalladium(11)

di-μ-bromo-bis[2-[(1,1-dimethylethyl)phenylphosphino]-2-methyl-propyl-C,P]dipalladium(11).

5. A process for preparing compounds of the formula (1), which comprises reacting a phosphine of the formula (11)

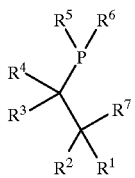

(II)

where R¹ to R⁶ are as defined above and R⁷ is hydrogen or deuterium, with a palladium salt of the formula (111), a palladium complex of the formula (IV) or an alkali metal palladate of the formula (V)

$$Pd\ Y_2 \qquad (III)$$

$$Pd\ Y_2L_2 \qquad (IV)$$

$$M_2[PdY_4] \qquad (V)$$

where Y is as defined above, M is sodium, potassium or lithium and L is 1,5-cyclooctadiene, acetoritrile or benzoritrile, in the presence of an organic solvent.

6. The process as claimed in claim 5, wherein the reaction is carried out at from 0 to 160° C.

7. The process as claimed in claim 5, wherein the reaction is carried out at from 10 to 150° C.

8. The process as claimed in claim 5, wherein the reaction is carried out at from 15 to 140° C.

9. The process as claimed in claim 5, wherein the phosphine of the formula (11) is used in a molar ratio of from 0.1 to 20 to the palladium compound of the formula (111), (IV) or (V).

10. The process as claimed in claim 9, wherein the phosphine of the formula (11) is used in a molar ratio of from 0.15 to 15 to the palladium compound of the formula (111), (IV) or (V).

11. The process as claimed in claim 9, wherein the phosphine of the formula (11) is used in a molar ratio of from 0.2 to 10, to the palladium compound of the formula (111), (IV) or (V).

12. The process as claimed in claim 5, wherein the solvents used are hydrocarbons.

13. A process for preparing compounds as claimed in claim 1, which comprises reacting a palladaphosphacyclobutane of the formula (1) with an anion of an inorganic or organic acid to give a sparingly soluble palladaphosphacyclobutane.

14. The process as claimed in claim 11, wherein the phosphine of the formula (II) is used in a molar ratio of from 0.8 to 1.2 to the palladium compound of the formula (III), (IV) or (V).

15. The process as in claim 12, wherein the hydrocarbons used are aromatic hydrocarbons.

16. The process as in claim 15, wherein the aromatic hydrocarbons used are toluene or xylenes.

* * * * *